United States Patent
Wadsworth et al.

(10) Patent No.: US 7,642,373 B2
(45) Date of Patent: Jan. 5, 2010

(54) RADICAL TRAP IN FLUORIDATION OF IODONIUM SALT

(75) Inventors: Harry John Wadsworth, Amersham (GB); David Arthur Widdowson, London (GB); Emmanuelle Wilson, London (GB); Michael Andrew Carroll, Newcastle upon Tyne (GB)

(73) Assignee: GE Healthcare Limited, Buckinghamshire (GB)

( * ) Notice: Subject to any disclaimer, the term of this patent is extended or adjusted under 35 U.S.C. 154(b) by 320 days.

(21) Appl. No.: 10/559,879

(22) PCT Filed: Dec. 17, 2004

(86) PCT No.: PCT/GB2004/005304
§ 371 (c)(1),
(2), (4) Date: Aug. 30, 2006

(87) PCT Pub. No.: WO2005/061415
PCT Pub. Date: Jul. 7, 2005

(65) Prior Publication Data
US 2006/0292060 A1 Dec. 28, 2006

(30) Foreign Application Priority Data
Dec. 23, 2003 (GB) .................. 0329716.5

(51) Int. Cl.
*C07B 59/00* (2006.01)

(52) U.S. Cl. .................................... 562/456

(58) Field of Classification Search ........ None
See application file for complete search history.

(56) References Cited

U.S. PATENT DOCUMENTS

2007/0092441 A1* 4/2007 Wadsworth et al. ........ 424/1.11

OTHER PUBLICATIONS

Chen et al. Synlett, 2000, No. 8, 1175-1177.*
Wuest, et.al., Pet-Corticosteroids as Potential Ligands for Mapping Brain Glucocorticoid Receptors (GR), J. Labelled Cpd. Radiopharm. 44. Suppl. 1 (2001) pp. S12-15.
Pike, et.al., "Reactions of cyclotron-produced [18F]fluoride with Diaryliodonium Salts-a Novel Single-step Route to No-carrier-added [18F]Fluoroarenes", J. Chem. Soc. Chem. Commun 1995 pp. 2215-2216.
Ochiai, et.al., alpha-Vinylation of 1,3-Dicarbonyl Compounds with Alkenyl(aryl)iodonium Tetrafluoroborates: Effects of Substituents on the Aromatic Ring and of Radical Inhibitors J. Org. Chem, 1997 vol. 62, pp. 2130-2138.
Shah, et.al. "The Synthesis of [18F]Fluoroarenes from the Reaction of Cyclotron-Produced [18F]Fluoride Ion with Diaryliodonium Salts" J. of the Chemical Society, Perkinn Transactions 1, Chemical society, Letchworth, GB vol. 13, 1998, pp. 2043-2046.
Lubinkowski, et.al., "Reactions of Diaryliodononium Salts with Sodium Alkoxides", J. Org. Chem., 1975, pp. 3010-3015.
PCT/GB2004/005304 Int'l Search report dated Apr. 2005.
GB0329716.5 Search report dated May 2005.

* cited by examiner

*Primary Examiner*—Daniel M Sullivan
*Assistant Examiner*—Yevegeny Valenrod
(74) *Attorney, Agent, or Firm*—Craig Bohlken

(57) ABSTRACT

Decomposition of iodonium salts by a free radical process has been identified as a significant factor in the observed yield variability of fluoridation reactions using said iodonium salts. Accordingly, the inclusion of a free radical trap in the reaction mixture blocks the radical chain decomposition pathway for iodonium salts such that only the reaction leading to fluoridation can occur and the yield of aryl fluoride becomes high and reproducible. The reaction may also be carried out on solid phase. In both the solution and the solid phase the preferred method of the present invention is radiofluoridation.

15 Claims, No Drawings

RADICAL TRAP IN FLUORIDATION OF IODONIUM SALT

TECHNICAL FIELD OF THE INVENTION

This application is a filing under 35 U.S.C. 371 of international application number PCT/GB2004/005304, filed Dec. 17, 2004, which claims priority to application No. 0329716.5 filed Dec. 23, 2003, in Great Britain the entire disclosure of which is hereby incorporated by reference.

The present invention relates to the field of radiochemistry and in particular to radiofluoridation. Specifically, the invention relates to a novel method for the radiofluoridation of iodonium salts wherein a free radical trap is included in the reaction mixture. An additional embodiment of the invention is the radiofluoridation of iodonium salts using a solid phase reaction.

DESCRIPTION OF RELATED ART

Aromatic nucleophilic substitution using the [$^{18}$F] fluoride anion to displace a suitable leaving group from an electron deficient aromatic ring is known as a method for the production of [$^{18}$F] fluoroarenes. The nucleophilic substitution reaction is illustrated below:

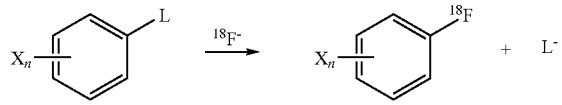

wherein $X_n$ represents between 1 and 4 electron withdrawing groups and L represents a suitable leaving group, e.g. fluoro, bromo, nitro, tertiary amino or iodo.

The radiochemistry is performed using a nucleophilic radiofluorinating agent such as [$^{18}$F] caesium fluoride or [$^{18}$F] potassium fluoride. Preferably, a phase transfer reagent such as Kryptofix™ is used when the radiofluorinating agent is [$^{18}$F] potassium fluoride. These radiofluorinating agents are prepared from cyclotron-produced no carrier added (NCA) [$^{18}$F] fluoride [as described by Aigbirhio et al 1995 J Fluorine Chem 70 p 279].

The use of this reaction in the radiofluoridation of iodonium salts has been reported by Pike et al [1995 J Chem Soc Chem Comm pp 2215-16] although with variable radiochemical yield (RCY). The reason for the variability in RCY was not understood. Subsequent reports from the same group [Shah et al 1998 J Chem Soc (Perkin Trans 1) pp 2043-6 and Martin-Santamaria et al 2000 Chem Comm pp 649-50] do not offer any further explanation for the variable RCY. More recently, Wüst et al [2001 J Labelled Cpd Radiopharm 44 pS12-3] reported that the reaction of phenyliodonium tosylate with [$^{18}$F] potassium fluoride (in the presence of Kryptofix™) yielded a very low amount of the desired [$^{18}$F] corticosteroid. Furthermore, the present applicants have found that radiofluoridation of iodonium salts according to the methods described above produces highly variable RCY (<5% to 40%) of the desired [$^{18}$F] aryl fluoride product. Such lack of reproducibility makes the use of iodonium salts for the synthesis of [$^{18}$F] aryl fluorides problematic.

SUMMARY OF THE INVENTION

Decomposition of iodonium salts by a free radical chain reaction process has been identified as a significant factor in the observed yield variability of fluoridation reactions using said iodonium salts. Accordingly, the inclusion of a free radical trap in the reaction mixture blocks the radical chain decomposition pathway for iodonium salts such that only the reaction leading to fluoridation can occur and the yield of aryl fluoride becomes reproducible. The reaction may also be carried out on solid phase. In both the solution and the solid phase the preferred method of the present invention is radiofluoridation.

DETAILED DESCRIPTION OF THE INVENTION

In a first aspect, the present invention relates to a method for the production of an aromatic fluorine-labelled compound comprising fluoridation of an iodonium salt with a fluoride ion source characterised in that the reaction mixture contains a free radical trap.

The "fluoride ion source" of the present invention is suitably selected from potassium fluoride, caesium fluoride and tetraalkylammonium fluoride. The preferred fluoride ion source of the invention is potassium fluoride which is most preferably activated with a phase transfer reagent, e.g. Kryptofix™.

The term "free radical trap" is defined as any agent that interacts with free radicals and inactivates them. A suitable free radical trap of the invention is selected from 2,2,6,6-Tetramethylpiperidine-N-Oxide (TEMPO), 1,2-diphenylethylene (DPE), ascorbate, para-amino benzoic acid (PABA), α-tocopherol, hydroquinone, di-t-butyl phenol, β-carotene and gentisic acid. Preferred free radical traps of the invention are TEMPO and DPE, with TEMPO being most preferred.

The reaction mixture usually contains at least 1 Mol % of the radical scavenger and preferably about 2-500 Mol %. A more preferred range is from about 10 to 400 Mol % of radical scavenger in the reaction mixture.

The term "iodonium salt" is defined in the present invention as a compound comprising an ion of the form $Y_2I^+$. Preferably, the iodonium salt of the invention is of Formula I:

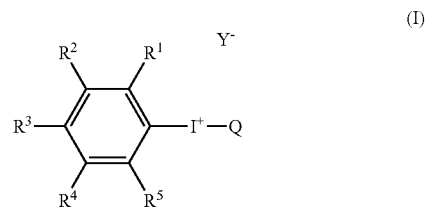

wherein:
Q is a precursor of the fluorine-labelled compound;
$R^1$-$R^5$ are independently selected from hydrogen, nitro, cyano, halogen, $C_{1-10}$ hydroxyalkyl, $C_{2-10}$ carboxyalkyl, $C_{1-10}$ alkyl, $C_{2-10}$ alkoxyalkyl, $C_{1-10}$ hydroxyalkyl, $C_{1-10}$ aminoalkyl, $C_{1-10}$ haloalkyl, $C_{6-14}$ aryl, $C_{3-12}$ heteroaryl, $C_{3-20}$ alkylaryl, $C_{5-12}$ arylene, $C_{2-10}$ alkenyl, $C_{2-10}$ alkynyl, $C_{1-10}$ acyl, $C_{7-10}$ aroyl, $C_{2-10}$ carboalkoxy, $C_{2-10}$ carbamoyl, $C_{2-10}$ carbamyl, or $C_{1-10}$ alkysulphinyl, or protected versions of any of these groups; or alternatively forms a four- to six-membered ring together with the R group to which it is adjacent, or protected versions thereof; and,
$Y^-$ is an anion selected from triflate, nonaflate, mesylate and hexaflate.

"Alkyl" used either alone or as part of another group is defined herein as any straight, branched or cyclic, saturated or unsaturated $C_nH_{2n+1}$ group, wherein unless otherwise specified n is an integer between 1 and 6.

"Aryl" used either alone or as part of another group is defined herein as any $C_{6-14}$ molecular fragment or group which is derived from a monocyclic or polycyclic aromatic hydrocarbon, or a monocyclic or polycyclic heteroaromatic hydrocarbon.

The term "halogen" means a group selected from fluorine, chlorine, bromine, and iodine, including isotopes thereof.

Suitable protection for $R^1$ to $R^5$ may be achieved using standard methods of protecting group chemistry. After the fluoridation is complete, any protecting groups may be removed by simple procedures which are also standard in the art. Suitable protection and deprotection methodologies may be found, for example, in Protecting Groups in Organic Synthesis, Theodora W. Greene and Peter G. M. Wuts, published by John Wiley & Sons Inc.

The iodonium salt of the invention is preferably solid support-bound as in Formula II:

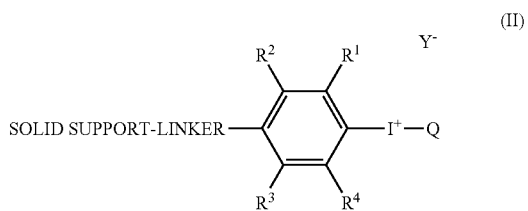

(II)

wherein

Q is a precursor of the fluorine-labelled compound; and, $R^1$-$R^4$ and $Y^-$ are as defined above for Formula I.

In the compound of Formula II, the "solid support" may be any suitable solid-phase support which is insoluble in any solvents to be used in the process but to which the linker can be covalently bound. Examples of suitable solid support include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a cartridge or on a microfabricated vessel.

In the compound of Formula II the "linker" may be any suitable organic group which serves to space the reactive site sufficiently from the solid support structure so as to maximise reactivity. Suitably, the linker comprises zero to four aryl groups and/or $C_{1-20}$ alkyl, $C_{2-20}$ alkoxyalkyl or $C_{1-20}$ haloalkyl, and optionally one or more additional substituents such as oxygen, halogen, amide or sulphonamide. The linker may also suitably be a polyethylene glycol (PEG) linker. Examples of such linkers are well known to those skilled in the art of solid-phase chemistry.

The precursor Q of Formulae I and II is preferably an aryl group optionally substituted by 1 to 5 substituents independently selected from nitro, cyano, halogen, $C_{1-10}$ hydroxyalkyl, $C_{2-10}$ carboxyalkyl, $C_{1-10}$ alkyl, $C_{2-10}$ alkoxyalkyl, $C_{1-10}$ hydroxyalkyl, $C_{1-10}$ aminoalkyl, $C_{1-10}$ haloalkyl, $C_{6-14}$ aryl, $C_{3-12}$ heteroaryl, $C_{3-20}$ alkylaryl, $C_{5-12}$ arylene, $C_{2-10}$ alkenyl, $C_{2-10}$ alkynyl, $C_{1-10}$ acyl, $C_{7-10}$ aroyl, $C_{2-10}$ carboalkoxy, $C_{2-10}$ carbamoyl, $C_{2-10}$ carbamyl, or $C_{1-10}$ alkylsulphinyl, or protected versions of any of these groups; or alternatively forms a four- to six-membered ring together with the R group to which it is adjacent, or protected versions thereof.

Especially preferred precursors Q are illustrated in Table I.

Whether the method of the invention is carried out in solution or on a solid phase, the fluorine-labelled compound of the invention is preferably an [$^{18}$F]-labelled compound and the fluoride ion source is preferably a source of $^{18}F^-$. Most preferably, the [$^{18}$F]-labelled compound is an [$^{18}$F]-labelled radiotracer, i.e. an [$^{18}$F]-labelled compound that is suitable for the detection by PET imaging of particular biological targets within a subject.

The [$^{18}$F]-labelled tracer is preferably selected from the compounds listed in the first column of Table I. The respective precursors of these [$^{18}$F]-labelled tracers are given in the second column of Table I, wherein $P^1$-$P^4$ are each independently hydrogen or a protecting group.

TABLE I

| $^{18}$F Compound | Precursor (Q) |
|---|---|
| (a) [$^{18}$F]-FDOPA | |
| (b) [$^{18}$F]-dopamine | |
| (c) [$^{18}$F]-5-fluorouracil | |

TABLE I-continued
| $^{18}$F Compound | Precursor (Q) |
|---|---|
| (d) [$^{18}$F]-mFBG 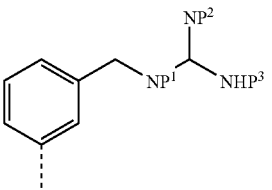 | |
| (e) [$^{18}$F]-FIBG 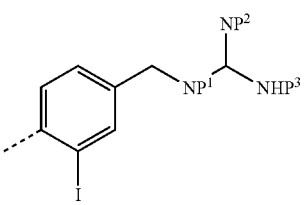 | |
| (f) [$^{18}$F]-fluorocarazolol 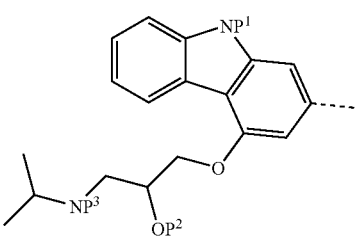 | |
| (g) [$^{18}$F]-pmPPF 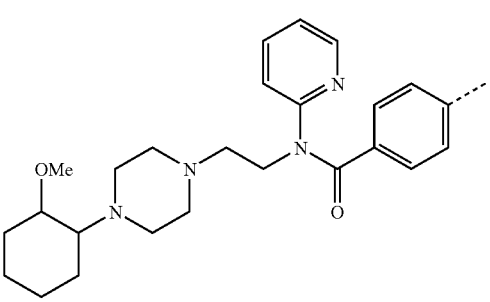 | |
| (h) [$^{18}$F]-altanaserine 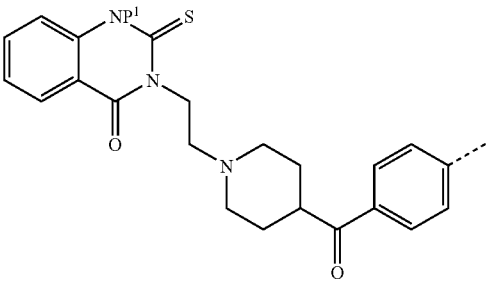 | |

TABLE I-continued

| ¹⁸F Compound | Precursor (Q) |
|---|---|

(i) [¹⁸F]-2-A85380

(j) [¹⁸F]-SC58125

(k) [¹⁸F]-Tyrosine (l) [¹⁸F]-Spiro-FBT (m) [¹⁸F]-FDP

TABLE I-continued

| ¹⁸F Compound | Precursor (Q) |
|---|---|
| (n) [¹⁸F]-flumanezil | |

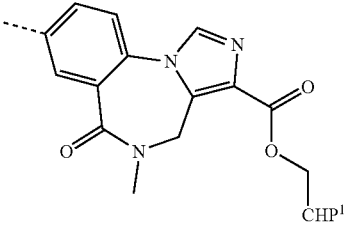

(o) [¹⁸F]-SFB labelling agent

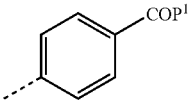

(p) [¹⁸F]-Formula III*

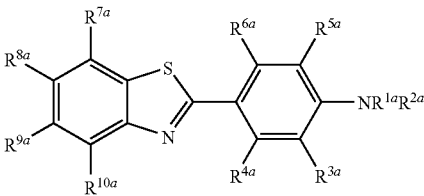

*for [¹⁸F]-Formula III: $R^{1a}$ and $R^{2a}$ are independently selected from hydrogen, a protecting group, $C_{1-6}$ alkyl, $C_{1-6}$ hydroxyalkyl, and $C_{1-6}$ haloalkyl; one of $R^{3a}$ to $R^{10a}$ is a bond to the ¹⁸F (in the case of the [¹⁸F]-compound) or one of $R^{3a}$ to $R^{10a}$ is a bond to the —I⁺— group in formula (Ia) (in the case of the precursor); and the other R groups are independently selected from hydrogen, halo, $C_{1-6}$ alkyl, $C_{1-6}$ haloalkyl, $C_{1-6}$ hydroxyalkyl, $C_{1-6}$ alkoxy, $C_{1-6}$ haloalkoxy, cyano, and nitro.

Most preferred [¹⁸F]-labelled compounds of the invention are [¹⁸F]-DOPA, [¹⁸F]-dopamine, and [¹⁸F]-fluorouracil, with [¹⁸F]-DOPA being especially preferred.

In a second aspect the present invention relates to an [¹⁸F]-labelled compound produced by the method of the invention.

BRIEF DESCRIPTION OF THE EXAMPLES

Example 1 describes the attempted fluoridation of diphenyliodonium triflate with potassium fluoride.

Example 2 describes the fluoridation method of Example 1 carried out in the presence of 2 mol % TEMPO.

Example 3 describes a known method of radiofluoridation of diphenyliodonium triflate which produced highly variable yields.

Example 4 describes the method of Example 3 carried out in the presence of 70 mole % TEMPO. The radiochemical yields obtained were considerably more consistent that those obtained in the absence of a radical scavenger suggesting that the variability observed with the method of Example 1 was at least partly as a result of the presence of free radicals.

Example 5 describes the method of Example 3 carried out in the presence of 50 mole % 1,2-diphenylethylene (1,2-DPE). The radiochemical yield was similar to that obtained with TEMPO demonstrating that alternative radical traps may also be used.

Examples 6-10 describe the radiofluoridation of a variety of other iodonium salts in the presence of varying amounts of TEMPO. A radiochemical yield similar to that obtained in Example 4 for radiofluoridation of diphenyliodonium triflate in the presence of TEMPO was obtained demonstrating that other iodonium salts can be radiofluoridated by the method of the invention.

Example 11 describes how the radiofluoridation reaction would be carried out in the case of iodonium salts immobilised onto a solid phase. As has been demonstrated with the solution phase method, it is anticipated that consistent radiochemical yields would also be obtained with this method.

Examples 12-15 describe the preparation of various solid-phase bound iodonium salts that may be fluoridated or radiofluoridated by the methods of the invention.

EXAMPLES

Comparative Example 1

Fluorination of diphenyliodonium triflate in the absence of radical scavenger

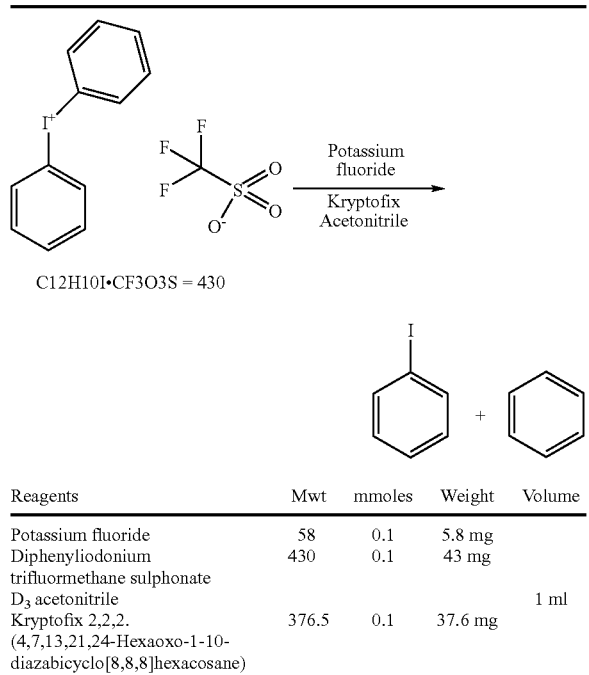

C12H10I·CF3O3S = 430

| Reagents | Mwt | mmoles | Weight | Volume |
|---|---|---|---|---|
| Potassium fluoride | 58 | 0.1 | 5.8 mg | |
| Diphenyliodonium trifluormethane sulphonate | 430 | 0.1 | 43 mg | |
| D$_3$ acetonitrile | | | | 1 ml |
| Kryptofix 2,2,2. (4,7,13,21,24-Hexaoxo-1-10-diazabicyclo[8,8,8]hexacosane) | 376.5 | 0.1 | 37.6 mg | |

Experimental

A solution of the potassium fluoride (5.8 mg, 0.1 mmol), 2,2,2-Kryptofix (37.6 mg, 0.1 mmol), in D$_3$-acetonitrile (0.5 ml) was prepared in an NMR tube. To this was added and diphenyl iodonium triflate (43 mg, 0.1 mmol) in D$_3$-acetonitrile (0.5 ml). The NMR's of the mixture were run ($^1$H, $^{13}$C and $^{19}$F NMR) and compared with the $^1$H $^{13}$C and $^{19}$F NMR (as appropriate) of the individual starting components. This indicated that on mixing of the components there was an immediate reaction converting the iodonium triflate to the fluoride. The reaction mixture was then heated to 80° C. for 60 min on an oil bath. The sample was removed from the hot oil, cooled to room temperature by plunging in cold water and the $^1$H $^{13}$C and $^{19}$F NMR determined. $^1$H, $^{13}$C and $^{19}$F NMR (as appropriate) of fluorobenzene, iodobenzene and benzene in D$_3$ acetonitrile were also run.

Results

From these NMR experiments it was clear that fluoride ion reacts immediately with the iodonium salt to give a compound which is completely different from the trifluoromethane salt. This compound was relatively stable at room temperature but slowly reacted. On heating the reaction the complex formed on mixing was converted to a mixture of benzene and iodobenzene.

Conclusion

The NMR data indicated that the first step of the reaction was rapid at room temperature with the iodonium ion disappearing immediately. The resulting intermediate (assumed to be the fluoride) was converted on heating to iodobenzene and benzene in what must be a reduction reaction.

Example 2

Fluorination of diphenyliodonium triflate in the presence of 2 mol % TEMPO

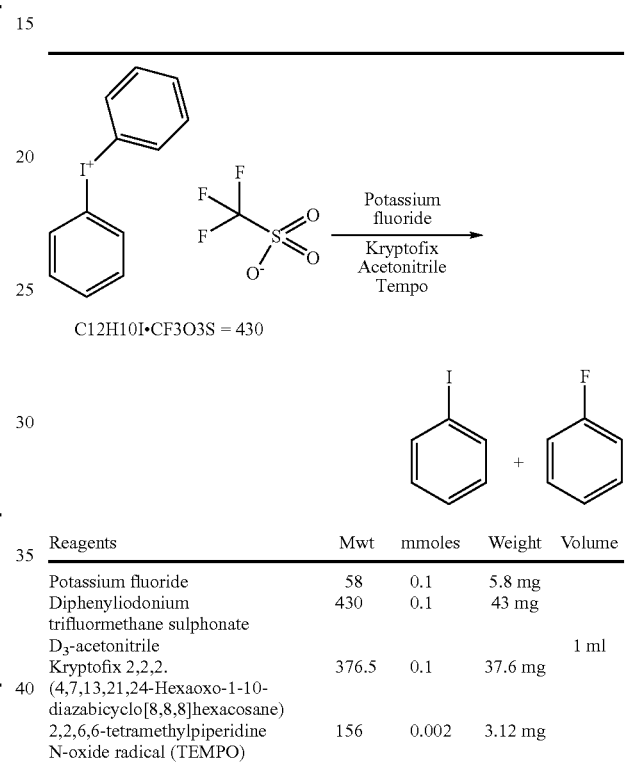

C12H10I·CF3O3S = 430

| Reagents | Mwt | mmoles | Weight | Volume |
|---|---|---|---|---|
| Potassium fluoride | 58 | 0.1 | 5.8 mg | |
| Diphenyliodonium trifluormethane sulphonate | 430 | 0.1 | 43 mg | |
| D$_3$-acetonitrile | | | | 1 ml |
| Kryptofix 2,2,2. (4,7,13,21,24-Hexaoxo-1-10-diazabicyclo[8,8,8]hexacosane) | 376.5 | 0.1 | 37.6 mg | |
| 2,2,6,6-tetramethylpiperidine N-oxide radical (TEMPO) | 156 | 0.002 | 3.12 mg | |

Experimental

The method of Example 5 was repeated with the addition to the reaction mixture of TEMPO (3.12 mg, 0.002 mmol).

Results

From these NMR experiments it was clear that fluoride ion reacts immediately with the iodonium salt to give a compound which is completely different from the trifluoromethane salt. This is identical to the previous reaction without TEMPO. The reaction was relatively stable at room temperature but slowly reacts. On heating the reaction the complex formed on mixing was converted to a mixture of fluorobenzene and iodobenzene.

Conclusion

The NMR data indicated that the first step of the reaction was rapid at room temperature with the iodonium ion disappearing immediately. The resulting intermediate was converted on heating to iodobenzene and fluorobenzene. The complete change in the course of the reaction on addition of TEMPO suggests that the reaction that converts the iodonium salt to benzene and iodobenzene is suppressed by the presence of a free radical terminator.

Comparative Example 3

Radiofluoridation of diphenyliodonium triflate in the absence of radical scavenger

[$^{18}$F] Fluoride in $^{18}$O enriched water (~0.3 ml) was loaded into a reaction vessel, to this was added kryptofix 222 (11.4 mg) and potassium carbonate (0.2 ml of a 0.1 M solution) in acetonitrile. The fluoride was dried by azeotropic drying. Following the completion of the drying process, a solution of diphenyliodonium triflate (ex Sigma-Aldrich Chemicals, 22.5 mg) in dry acetonitrile (1 ml) was added to the dry fluoride. The mixture was heated at 95° C. for 15 minutes before being cooled in a stream of compressed air. The product was transferred to a sealed collection vial and the reaction analysed by HPLC.

Randiochemical purity (RCP) and RCY values obtained are presented in the table below:

| Reaction No | RCP | RCY |
| --- | --- | --- |
| 1 | 0 | 0 |
| 2 | 10 | 5 |
| 3 | 64 | 24 |
| 4 | 50 | 28 |
| 5 | 5 | 4 |
| 6 | 41 | 30 |
| 7 | 9 | 5 |
| 8 | 60 | 40 |
| 9 | 15 | 11 |
| 10 | 4 | 3 |
| 11 | 6 | 4 |
| 12 | 4 | 3 |
| 13 | 0 | 0 |
| 14 | 3 | 2 |
| 15 | 3 | 3 |
| 16 | 0 | 0 |
| 17 | 18 | 10 |
| 18 | 7 | 4 |
| 19 | 22 | 1 |
| 20 | 23 | 18 |
| 21 | 49 | 23 |
| 22 | 22 | 9 |

Example 4

Radiofluoridation of diphenyliodonium triflate in the presence of 70 mole % TEMPO The same reaction as described in Example 3 was carried out in the presence of 70 Mol % TEMPO.

The RCP and RCY values obtained are presented in the table below:

| Reaction No | RCP | RCY |
| --- | --- | --- |
| 28 | 96 | 45 |
| 29 | 94 | 57 |
| 30 | 95 | 45 |
| 31 | 91 | 70 |
| 32 | 97 | 47 |
| 33 | 97 | 41 |
| 34 | 82 | 49 |

Example 3

Radiofluoridation of diphenyliodonium triflate in the presence of 50 mol % 1,2-DPE The same reaction as described in Example 3 was carried out in the presence of 50 Mol % of 1,2-DPE.

The RCP and RCY values obtained are presented in the table below:

| Reaction No | RCP | RCY |
| --- | --- | --- |
| 35 | 64 | 37 |

Example 4

Radiofluoridation of (2-methyl-4-methoxyphenyl)phenyliodonium trifluoroacetate in the presence of 93 mol % TEMPO

[$^{18}$F]-fluoride in $^{18}$O enriched water (~0.4 ml) was loaded into the reaction vessel, to this was added a mixture of a solution of Kryptofix (17.9 mg, ex Sigma-Aldrich Chemicals) in acetonitrile (1 ml) and potassium carbonate (0.2 ml of a 0.1 M aqueous solution). The fluoride was dried by azeotropic drying. Following the completion of the drying process, a solution of (2-methyl 4-methoxyphenyl)phenyliodonium trifluoracetate (21.2 mg) and TEMPO (ex Sigma-Aldrich Chemicals) (7.8 mg) in acetonitrile (1 ml) was added to the dry fluoride. The mixture was heated at 95° C. for 15 minutes before being cooled in a stream of compressed air. The product was transferred to a sealed collection vial and the reaction analysed by HPLC.

The RCP and RCY values obtained are presented in the table below:

| Reaction No | RCP | RCY |
| --- | --- | --- |
| 36 | 85 | 52 |
| 37 | 63 | 45 |

Example 5

Radiofluoridation of 2-Methoxyphenyl 4'methoxy-2'methyliodonium trifluoroacetate in the presence of 100 mol % TEMPO The method used was as described above in Example 6 except that 2-Methoxyphenyl 4'methoxy-2'methyliodonium trifluoroacetate was used in place of (2-methyl-4-methoxyphenyl)phenyliodonium trifluoroacetate.

The RCP and RCY values obtained are presented in the table below:

| Reaction No | RCP | RCY |
| --- | --- | --- |
| 38 | 58 | 28 |
| 39 | 88 | 59 |

Example 8

Radiofluoridation of 2-Methoxyphenyl 5'-benzoyloxy-4-methoxy-2-methyl trifluoroacetate in the presence of 100 mol % TEMPO The method used was as described above in Example 6 except that 2-Methoxyphenyl 5'-benzoyloxy-4-methoxy-2-methyl trifluoroacetate was used in place of (2-methyl-4-methoxyphenyl)phenyliodonium trifluoroacetate.

| Reaction No | RCP | RCY |
|---|---|---|
| 40 | 25 | 17 |
| 41 | 70 | 28 |

Example 9

Radiofluoridation of Phenyl 5-benzoyloxy-4-methoxy-2-methyliodonium trifluoroacetate in the presence of 324 mol % TEMPO The method used was as described above in Example 6 except that Phenyl 5-benzoyloxy-4-methoxy-2-methyliodonium trifluoroacetate was used in place of (2-methyl-4-methoxyphenyl)phenyliodonium trifluoroacetate.

| Reaction No | RCP | RCY |
|---|---|---|
| 42 | 86 | 50 |

Example 10

Radiofluoridation of (1-methoxypyrazole)(2-methoxyphenyl)iodonium trifluoroacetate in the presence of 50 mol % TEMPO The method used was as described above in Example 6 except that (1-methoxypyrazole)(2-methoxyphenyl)iodonium trifluoroacetate was used in place of (2-methyl-4-methoxyphenyl)phenyliodonium trifluoroacetate.

| Reaction No | RCP | RCY |
|---|---|---|
| 43 | 81 | 61 |

Example 11

Radiofluoridation of resin bound iodonium salt in the presence of 50 mol % TEMPO TEMPO (ex Sigma-Aldrich Chemicals) (7.8 mg) in acetonitrile (0.5 ml) is added to the iodonium resin (98.3 mg) and then heated to 100° C. and then allowed to cool to ambient temperature. [$^{18}$F]-fluoride in $^{18}$O enriched water ((~0.4 ml) is loaded into a separate reaction vessel, to this is added a mixture of a solution of Kryptofix (17.9 mg, ex Sigma-Aldrich Chemicals) in acetonitrile (1 ml) and potassium carbonate (0.2 ml of a 0.1 M aqueous solution). The fluoride is dried by azeotropic drying. Following the completion of the drying process, TEMPO (9.6 mg) in dry acetonitrile (1.5 ml) is added and the mixture heated to 80° C. for ten minutes, then cooled by a stream of compressed air. The solution is then added to the resin and the reaction heated at 80° C. for 10 minutes.

The vessel is cooled to 30° C. and the product transferred into a product vial. The reaction is analysed by HPLC.

Example 12

Preparation of 6-(4-phenyliodoniumphenoxy)hexanoic acid-amino methyl polystyrene amide trifluoroacetate salt The synthetic route is illustrated below:

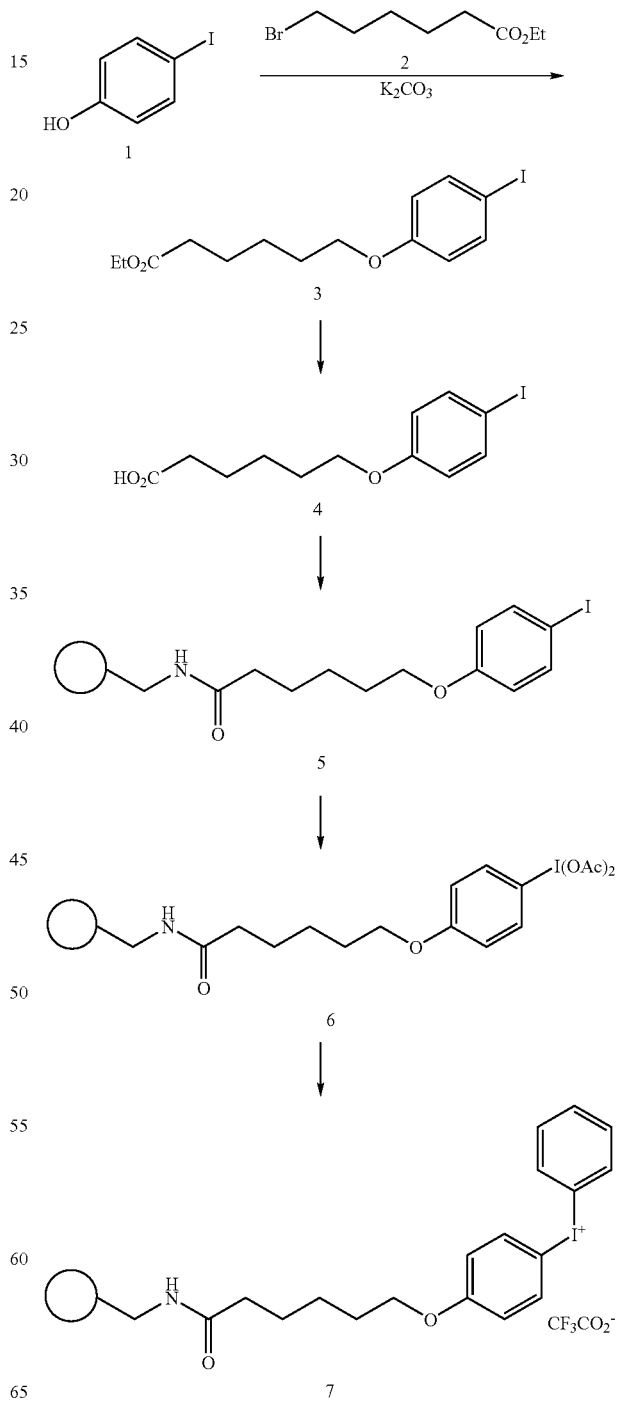

(a) Preparation of ethyl 6-(4-iodophenoxy)hexanoate (3)

Ethyl 6-bromohexanoate (5.55 g, 25 mmol) in acetone (100 ml) was treated with 4-iodophenol (5.55 g, 25 mmol) and potassium carbonate (6.9 g 50 mmol). The stirred reaction was heated under reflux for 60 h. The reaction was then allowed to cool and the reaction concentrated in vacuum to a gum. The reaction was them partitioned between ethyl acetate (100 ml) and water (100 ml). The ethyl acetate layer was separated dried, over magnesium sulfate and concentrated in vacuo to give a colourless gum (8.71 g, 24.1 mmol, 96%), $\delta_H$ (CDCl$_3$) 1.26 (3H, t, CO$_2$CH$_2$CH$_3$), 1.46-1.81 (6H, m, 3,4,5-CH$_2$), 2.33 (2H, t, 2-CH$_2$), 3.91 (2H, t, 6-CH $_2$), 4.13 (2H, q, CO$_2$CH$_2$CH$_3$), 6.66 (2H, dd, 2,6-ArH), 7.53 (2H, dd, 3,5-ArH), $\delta_H$ (CDCl$_3$) 14.20, 24.60, 25.53, 28.75, 34.14, 60.20, 67.67, 82.44, 116.83,1 38.09, 158.84, and 173.52.

(b) Preparation of 6-(4-iodophenoxy)hexanoic acid (4)

Ethyl 6-(4-iodophenoxy)hexanoate (3.62 g, 10 mmol), in ethanol (30 ml), water (30 ml) was treated with sodium hydroxide (1 g, 25 mmol) and the reaction was stirred under reflux for 3 h. The reaction was then allowed to cool and concentrated in vacuum to a solid. The solid was then treated cautiously with ethyl acetate (100 ml) and 1N hydrochloric acid (100 ml) and the reaction stirred at room temperature for 10 min. The ethyl acetate layer was separated dried over sodium sulfate and concentrated in vacuum to give a pale yellow solid (3.11 g, 9.3 mmol, 93%), $\delta_H$ (CDCl$_3$) 1.48-1.82 (6H, m, 3,4,5-CH$_2$), 2.40 (2H, t, 2-CH$_2$), 3.91 (2H, t, 6-CH$_2$O), 6.67 (2H, dd, 2,6-ArH), 7.53 (2H, dd, 3,5-ArH), $\delta_c$ (CDCl$_3$) 24.31, 25.50, 38.75, 33.89, 82.54, 116.87, 138.14, 158.83 and 179.97

(c) Preparation of 6-(4-iodophenoxy)hexanoic acid-aminomethyl polystyrene resin amide (5)

Aminomethyl polystyrene resin (4.28 g, 6 mmol) in dichloromethane (30 ml) was treated with 6-(4-iodophenoxy)hexanoic acid (2.672 g, 8 mmol), diisopropylethylamine (2.322 g 18 mmol) and diphenylphosphoryl chloride (1.888 g, 8 mmol). The reaction was placed on a blood wheel and kept under agitation for 18 h. The reaction was then filtered and the resin washed with dichloromethane (100 ml). The resin was then dried in vacuum to give the desired aryl iodide substituted resin (6.3039 g). Found C 75.36%, H 6.62%, N 1.52%, I 11.12%

(d) Oxidation of 6-(4-iodophenoxyhexanoic acid-aminomethyl polystyrene resin amide with peracetic acid (6)

6-(4-iodophenoxy)hexanoic acid-aminomethyl polystyrene resin (1 g, 1 mmol) in dichloromethane (15 ml) was treated with peracetic acid (5 ml). The reaction was stirred with an overhead stirrer for 18 h at room temperature. The reaction was then filtered and the resin washed with dichloromethane (100 ml). The resin was then dried in vacuum to give a yellow solid.

(e) Reaction of 6-(4-diacetoxyiodophenoxy)hexanoic acid-aminomethyl polystyrene amide with tri-n-butylphenyltin and trifluoroacetic acid to give 6-(4-phenyliodoniumphenoxy)hexanoic acid-amino methyl polystyrene amide trifluoroacetate salt (resin bound iodonium salt 1) (7)

6-(4-diacetoxyiodophenoxy)hexanoic acid-aminomethyl polystyrene amide (1 g, 0.5 mmol), in dichloromethane (10 ml) was cooled to –40 C was treated with tri-n-butyl phenyl tin (367 mg, 1 mmol). The stirred reaction was then treated with trifluoroacetic acid (288 mg 2.0 mmole) and allowed to warm to room temperature over 2 h. The resin was washed thoroughly with dichloromethane. Found: C 70.47%, H 5.81%, N 1.53%, I 11.59%, F 3.78% $\delta_F$ (CDCl$_3$)-78.

Example 13

Preparation of 6-(2-((S)3-methoxycarbonyl-3-N-t-butoxycarbamyl-4,5-di(t-butoxycarbonyloxy)phen-6-yl)phenoxy)hexanoic acid-amino methyl polystyrene amide trifluoroacetate salt The synthetic route is illustrated below:

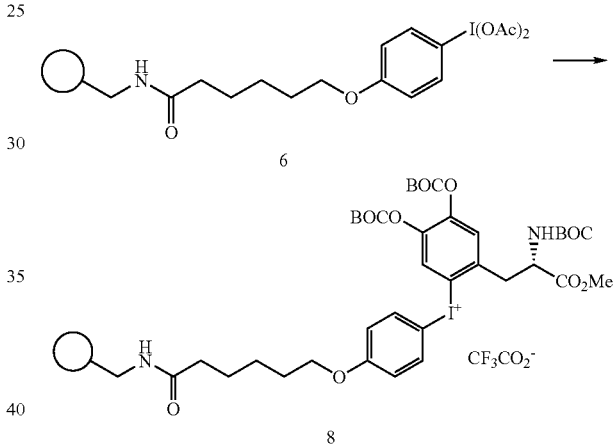

6-(4-diacetoxyiodophenoxy)hexanoic acid-aminomethyl polystyrene amide, in dichloromethane is cooled to –40 C is treated with methyl N-t-butoxycarbonyl-3,4-di(t-butoxycarbonyloxy)-6-trimethylstannyphenylalnine. The stirred reaction is then treated with trifluoroacetic acid and allowed to warm to room temperature over 2 h. The resin is washed thoroughly with dichloromethane

Example 14

Preparation of 6-(4-phenyliodonium-phenoxy)undecanoic acid-aminomethyl polystyrene amide trifluoroacetate salt The synthetic route is illustrated below:

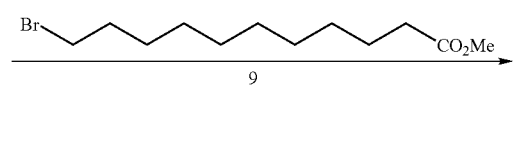

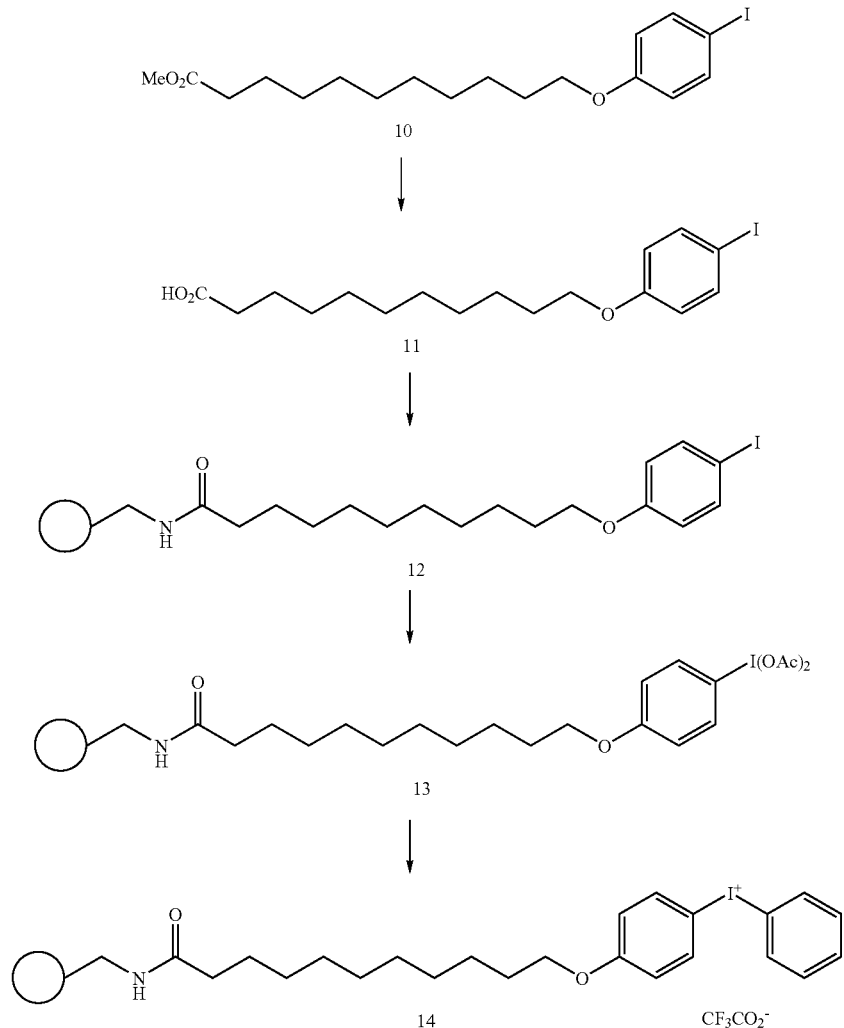

(a) Preparation of methyl 11-(4-iodophenoxy)undecanoate (10)

Methyl 11-bromoundecanoate (10 g, 35.8 mmmol), in acetone (150 ml) was treated with 4-iodophenol (7.88 g, 35.8 mmol) and potassium carbonate (9.88 g 71.6 mmol). The stirred reaction was heated at reflux for 48 h. The reaction was then allowed to cool and the reaction concentrated in vacuo to a gum. The reaction was then partitioned between ethyl acetate (150 ml) and water (150 ml). The ethyl acetate layer was separated dried, over sodium sulfate and concentrated in vacuo to solid. The solid was dissolved in diethyl ether (100 ml) and petroleum ether 60-80 C (100 ml) added. The solution was concentrated in vacuum to a volume of 100 ml. The solution was set aside and allowed to crystallise. The product was collected by filtration and dried in vacuum to give 12.22 g of solid. The mother liquors were concentrated to ~20 ml and allowed to crystallise. A further 0.81 g of solid was collected by filtration. The two solids were combined to give the desired product (13.03 g, 86%) $\delta_H$ (CDCl$_3$) 1.29-1.78 (16H, m, 3,4,5,6,7,8,9,10-CH$_2$), 2.30 (2H, t, 2-CH$_2$), 3.86 (3H, s, CO$_2$CH$_3$), 3.90 (2H, t, 11-CH$_2$), 6.66 (2H, dd, 2,6-ArH), 7.53 (2H, dd, 3,5-ArH), $\delta_C$(CDCl$_3$) 24.90, 25.93, 29.09, 29.18, 29.30, 29.42, 34.07, 51.42, 68.06, 82.35, 116.90, 138.11, 158.98, and 174.33.

(b) Hydrolysis of methyl 11-(4-iodophenoxy)undecanoate (11)

Methyl 11-(4-iodophenoxy)undecanoate (10 g, 23.9 mmmol), in methanol (100 ml) was treated with sodium hydroxide (2.4 g, 60 mmol). The stirred reaction was heated at 40 C for 60 h. The reaction contained a heavy white precipitate at the end of the reaction. The reaction was then cooled to room temperature and concentrated in vacuo. The resulting solid was then treated with 1N hydrochloric acid (250 ml) and ethyl acetate (250 ml) and stirred vigorously until the solid had dissolved. The organic phase was separated dried over sodium sulfate and concentrated in vacuo to give 11-(4-iodophenoxy)-undecanoic acid (9.55 g, 23.6 mmol, 98%) $\delta_H$ (CDCl$_3$)1.29-1.78 (16H, m, 3,4,5,6,7,8,9,10-CH$_2$), 2.35 (2H, t, 2-CH$_2$), 3.90 (2H, t, 11-CH$_2$), 6.66 (2H, dd, 2,6-ArH), 7.53 (2H, dd, 3,5,-ArH), $\delta_c$(CDCl$_3$) 24.61, 25.92, 28.98, 29.08, 29.16, 29.27, 29.41, 34.02, 68.08, 82.37, 116.90, 138.11, 158.97, and 180.18.

(c) Preparation of 11-(4-iodophenoxy)undecanoic acid-aminomethyl polystyrene resin amide (12)

Aminomethyl polystyrene resin (4.28 g, 6 mmol) in dichloromethane (30 ml) was treated with 11-(4-iodophenoxy)undecanoic acid (3.12 g, 8 mmol), diisopropylethylamine (2.32 g 18 mmol) and diphenylphosphoryl chloride (1.89 g, 8 mmol). The reaction was placed on a blood wheel and kept under agitation for 18 h. The reaction was then filtered and the resin washed with dichloromethane (100 ml). The resin was then dried in vacuo to give the desired aryl iodide substituted resin (6.30 g).

(d) Oxidation of 11-(4-iodophenoxy)undecanoic acid-amino methyl polystyrene resin amide with peracetic acid (13)

11-(4-iodophenoxy)undecanoic acid-amino polystyrene resin (1 g, 1 mmol) in dichloromethane (15 ml) was treated with peracetic acid (5 ml). The reaction was stirred with an overhead stirrer for 18 h at room temperature. The reaction was then filtered and the resin washed with dichloromethane (500 ml). The resin was then dried in vacuum to give a yellow solid (990 mg).

(e) Reaction of 6-(4-diacetoxyiodo-phenoxy)undecanoic acid-aminomethyl polystyrene amide with tri-n-butylphenyltin and trifluoroacetic acid to give 6-(4-Phenyliodonium-phenoxy)undecanoic acid-aminomethyl polystyrene amide Trifluoroacetate Salt (14)

6-(4-diacetoxyiodophenoxy)undecanoic acid-aminomethyl polystyrene amide in dichloromethane is cooled to −40 C is treated with tri-n-butylphenyltin. The stirred reaction is then treated with trifluoroacetic acid and allowed to warm to room temperature over 2 h. The resin is washed thoroughly with dichloromethane.

Example 15

Preparation of 6-(4-(phenyliodonium)phenoxy)hexanoic acid-aminomethyl amide polystyrene trifluoroacetate salt The synthetic route is illustrated below:

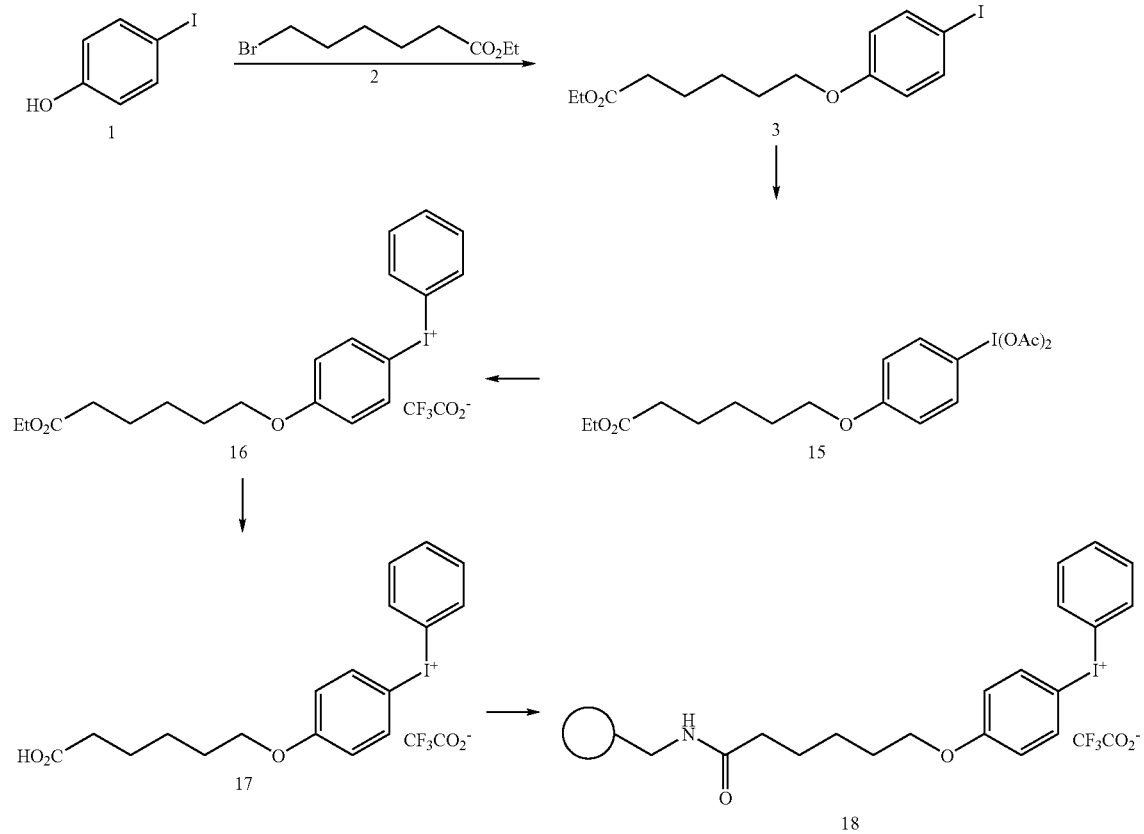

(a) Peracetic acid oxidation of ethyl 6-(4-iodophenoxy)hexanoate (15)

Ethyl 6-(4-iodophenoxy)hexanoate (3.62 g, 10 mmol) was treated with peracetic acid (39%) (5 ml) and dichloromethane (15 ml) on an ice bath with stirring. The reaction was allowed to warm to room temperature whilst stirred over a period of 2 h. The reaction initially darkened but after 30 min became a pale yellow colour. The reaction was then partitioned between dichloromethane (30 ml) and water (30 ml). The dichloromethane layer was separated dried over magnesium sulfate and concentrated under high vacuum to a gum (4.53 g, 9.4 mmol, 94%) $\delta_H$ (CDCl$_3$) 1.26 (3H, t, CO$_2$CH$_2$CH$_3$), 1.51-1.85 (6H, m, 3,4,5-CH$_2$), 2.00 (6H, s, 2×CH$_3$CO$_2$), 2.34 (2H, t, 2-CH$_2$), 4.01 (2H, t, 6-CH$_2$), 4.14 (2H, q, CO$_2$CH$_2$CH$_3$), 6.94 (2H, dd, 2,6-ArH), 8.00 (2H, dd, 3,5-ArH); $\delta_C$ (CDCl$_3$) 14.18, 20.31, 24.52, 25.47, 28.61, 34.10, 60.24, 68.27, 111.34, 116.98, 137.07, 161.63, 173.67, and 176.32.

(b) Reaction of ethyl 6-(4-diacetoxyiodophenoxy)hexanoate with tri-n-butylphenyltin (16)

Ethyl 6-(4-diacetoxyiodophenoxy)hexanoate (905 mg, 2.5 mmol) in dichloromethane (10 ml) was cooled to −40 C and treated with tri-n-butylphenyltin (954 mg, 2.6 mmole) and trifluoroacetic acid (592 mg, 5.2 mmole). The reaction was stirred for 1 h whilst it was allowed to warm to room temperature. The reaction was concentrated under high vacuum to a give a gum (2.4 g) containing product and tri-n-butyltrifluoroacetate.

(c) Hydrolysis of Ethyl 6-(4-phenyl iodonium phenoxy)hexanoate trifluoroacaetate Salt with Aqueous Trifluoroacetic Acid (17)

Ethyl 6-(4-phenyliodoniumphenoxy)hexanoate (350 mg, 0.729 mmol) in water/trifluoroacetic acid 1:1 (10 ml) was stirred for 18 h at 80 C. The reaction was then concentrated in high vacuum to give the products as a gum. The gum was stirred with petroleum ether and the iodonium salt was freed of the solution of the tri-n-butyltin trifluoroacetate from the previous step by decanting off the supernatant solution.

(d) Coupling of 6-(4-(phenyliodonium)phenoxy)hexanoic acid trifluoroacetate salt with aminomethyl polystyrene resin (18)

To aminomethyl polystyrene resin (714 mg) in dichloromethane (15 ml) was added crude 6-(4-(phenyliodonium) phenoxy)hexanoic acid trifluoroacetate salt (1.2 g, 1.25 mmol) diphenylphosphinic chloride (295 mg, 1.25 mmole) and diisopropylethylamine (387 mg, 3.0 mmole). The reaction was shaken on a blood wheel overnight and then washed with methanol/dichloromethane (100 ml) followed by dichloromethane (100 ml). The resin was then dried in vacuo to give the resin as a solid (0.95 g).

Found: C 72.85%, H 62.6%, N 1.53%,17.49%, F 1.67%.

What is claimed is:

1. A method for the production of an aromatic fluorine-labelled compound comprising fluoridation of an iodonium salt with a fluoride ion source characterised in that the reaction mixture contains a free radical trap; wherein the free radical trap is selected from a group consisting of 2,2,6,6-Tetramethylpiperidine-N-Oxide, 1,2-diphenylethylene, ascobate, para-amino benzoic acid, α-tocopherol, hydroquinone, si-t-butyl phenol, β-carotene and gentisic acid.

2. The method of claim 1 wherein the free radical trap is 2,2,6,6-Tetramethylpiperidine-N-Oxide or 1,2-diphenylethylene.

3. The method of claim 1 wherein the fluoride ion source is selected from potassium fluoride, caesium fluoride and tetraalkylammonium fluoride.

4. The method of claim 3 wherein the fluoride ion source is potassium fluoride and Kryptofix™ is used to activate the fluoride ion.

5. The method of claim 1 wherein the iodonium salt is of Formula I:

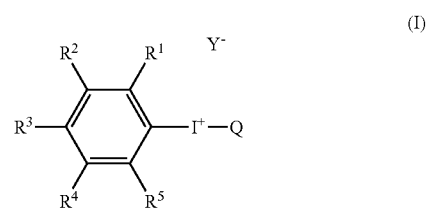

wherein:

Q is a precursor of the fluorine-labelled compound;

$R^1$-$R^5$ are independently selected from hydrogen, nitro, cyano, halogen, $C_{1-10}$ hydroxyalkyl, $C_{2-10}$ carboxyalkyl, $C_{1-10}$ alkyl, $C_{2-10}$ alkoxyalkyl, $C_{1-10}$ hydroxyalkyl, $C_{1-10}$ aminoalkyl, $C_{1-10}$ haloalkyl, $C_{6-14}$ aryl, $C_{3-12}$ heteroaryl, $C_{3-20}$ alkylaryl, $C_{5-12}$ arylene, $C_{2-10}$ alkenyl, $C_{2-10}$ alkynyl, $C_{1-10}$ acyl, $C_{7-10}$ aroyl, $C_{2-10}$ carboalkoxy, $C_{2-10}$ carbamoyl, $C_{2-10}$ carbamyl, or $C_{1-10}$ alkylsulphinyl, or protected versions of any of these groups; or alternatively forms a four- to six-membered ring together with the R group to which it is adjacent, or protected versions thereof; and, Y$^-$ is an anion selected from triflate, nonaflate, mesylate and hexaflate.

6. The method of claim 1 wherein the iodonium salt is solid support-bound as in Formula II:

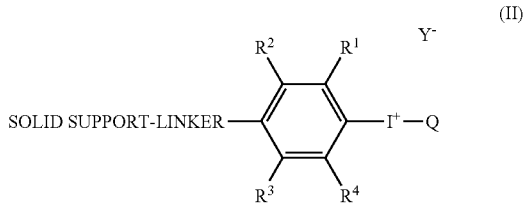

wherein:

Q is a precursor of the fluorine-labelled compound; and, $R^1$-$R^4$ and Y$^-$ are independently selected from hydrogen, nitro, cyano, halogen, $C_{1-10}$ hydroxyalkyl, $C_{2-10}$ carboxyalkyl, $C_{1-10}$ alkyl, $C_{2-10}$ alkoxyalkyl, $C_{1-10}$ hydroxyalkyl, $C_{1-10}$ aminoalkyl, $C_{1-10}$ haloalkyl, $C_{6-14}$ aryl, $C_{3-12}$ heteroaryl, $C_{3-20}$ alkylaryl, $C_{5-12}$ arylene, $C_{2-10}$ alkenyl, $C_{2-10}$ alkynyl, $C_{1-10}$ acyl, $C_{7-10}$ aroyl, $C_{2-10}$ carboalkoxy, $C_{2-10}$ carbamoyl, $C_{2-10}$ carbamyl, or $C_{1-10}$ alkylsulphinyl, or protected versions of any of these groups; or alternatively forms a four- to six-membered ring together with the R group to which it is adjacent, or protected versions thereof; and, Y$^-$ is an anion selected from triflate, nonaflate, mesylate and hexaflate.

7. The method claim 5 wherein Q is an aryl group optionally substituted by 1 to 5 substituents independently selected from nitro, cyano, halogen, $C_{1-10}$ hydroxyalkyl, $C_{2-10}$ carboxyalkyl, $C_{1-10}$ alkyl, $C_{2-10}$ alkoxyalkyl, $C_{1-10}$ hydroxyalkyl, $C_{1-10}$ aminoalkyl, $C_{1-10}$ haloalkyl, $C_{6-14}$ aryl, $C_{3-12}$ heteroaryl, $C_{3-20}$ alkylaryl, $C_{5-12}$ arylene, $C_{2-10}$ alkenyl, $C_{2-10}$ alkynyl, $C_{1-10}$ acyl, $C_{7-10}$ aroyl, $C_{2-10}$ carboalkoxy, $C_{2-10}$ carbamoyl, $C_{2-10}$ carbamyl, or $C_{1-10}$ alkylsulphinyl, or protected versions of any of these groups; or alternatively forms a fourto six-membered ring together with the R group to which it is adjacent, or protected versions thereof.

8. The method of claim 1 wherein the fluorine-labelled compound is an [$^{18}$F]-labelled compound and the fluoride ion source is a source of $^8$F$^-$.

9. The method of claim 8 wherein the [$^{18}$F]-labelled compound is [$^{18}$F]-FDOPA.

10. The method of claim 5 wherein the precursor is of Formula Ia:

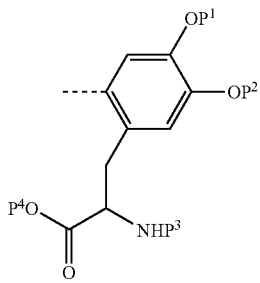

(Ia)

wherein P$^1$, P$^2$, P$^3$, and P$^4$ are each independently hydrogen or a protecting group;
said method producing the labelled compound of Formula IIa:

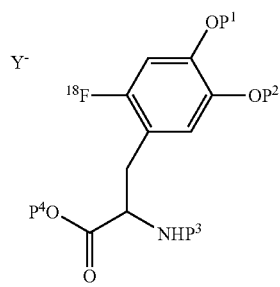

(IIa)

wherein P$^1$, P$^2$, P$^3$, and P$^4$ are each independently hydrogen or a protecting group and Y$^-$ is an anion, preferably trifluoromethylsulphonate (triflate) anion.

11. The method of claim wherein the [$^{18}$F]-labelled compound is [$^{18}$F]-dopamine.

12. The method of claim 5 wherein the precursor is of Formula Ib:

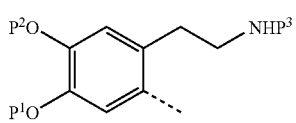

(Ib)

wherein P$^1$, P$^2$, and P$^3$ are each independently hydrogen or a protecting group;
said method producing the labelled compound of Formula IIb:

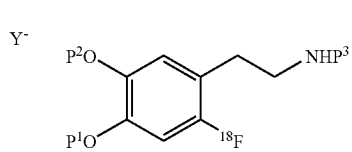

(IIb)

wherein P$^1$, P$^2$, and P$^3$ are each independently hydrogen or a protecting group and Y$^-$ is an anion, preferably trifluoromethylsulphonate (triflate) anion.

13. The method of claim 8 wherein the [$^{18}$F]-labelled compound is [$^{18}$F]-uracil.

14. The method of claim 5 wherein the precursor is of Formula Ic:

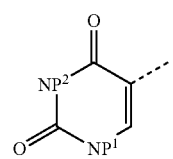

Ic wherein P$^1$ and P$^2$ are each independently hydrogen or a protecting group;
said method producing the labelled compound of Formula IIc:

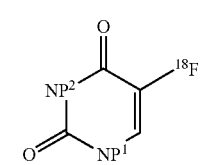

IIc wherein P$^1$ and P$^2$ are each independently hydrogen or a protecting group and Y$^-$ is an anion, preferably trifluoromethylsulphonate (triflate) anion.

15. The method of claim 8, further comprising:
(i) removal of excess $^{18}$F$^-$, for example by ion-exchange chromatography; and/or
(ii) removal of the protecting groups; and/or
(iii) removal of organic solvent; and/or
(iv) formulation of the resultant compound as an aqueous solution.

* * * * *

UNITED STATES PATENT AND TRADEMARK OFFICE
CERTIFICATE OF CORRECTION

PATENT NO. : 7,642,373 B2 Page 1 of 1
APPLICATION NO. : 10/559879
DATED : January 5, 2010
INVENTOR(S) : Wadsworth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 516 days.

Signed and Sealed this

Sixteenth Day of November, 2010

David J. Kappos
*Director of the United States Patent and Trademark Office*